US00PP14247P29

(12) United States Plant Patent
Bradford

(10) Patent No.: US PP14,247 P2
(45) Date of Patent: Oct. 21, 2003

(54) PLUM TREE NAMED 'AUGUST YUMMY'

(50) Latin Name: *Prunus salicina*
Varietal Denomination: August Yummy®

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/300,603

(22) Filed: Nov. 21, 2002

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Susan B. McCormick

(57) ABSTRACT

The present invention relates to a plum tree, *Prunus salicina,* and more particularly to a new and distinct variety broadly characterized by a medium size, vigorous, hardy, self-unfruitful, heavy blooming, pollen abundant, and usually productive tree that may be cross pollinized by 'Blackamber' (unpatented). The fruit matures under the ecological conditions described during mid August, with first picking on Aug. 11, 2002, but will hang on the tree for nearly twenty more days. The fruit is uniformly large in size, dark red in skin color, clingstone in type, yellow with some red bleeding in flesh color, very firm and crisp in texture, very good in flavor, and holds well in cold storage for more than thirty days. The variety was developed as a first generation cross using 'Grand Rosa' (U.S. Plant Pat. No. 1,756) plum as the selected seed parent and an undetermined plum as the pollen parent.

1 Drawing Sheet

Botanical classification: *Prunus salicina.*
Variety denomination: 'August Yummy®'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'August Yummy®'. Yummy® is a U.S. Trademark, application Ser. No. 75/618,722, owned by Johnny Appleseed Holdings Limited, Saint Georges Road South RD2, Hastings, New Zealand. Permission to use has been granted to the applicant by contract.

During a typical blooming season I isolate as seed parents both individual and groups of different plum trees by covering them with screen houses. A hive of bees is placed inside each such house and bouquets to provide pollen from different plum, apricot, and plum-apricot hybrid trees are placed near the trees approximately every three days for the duration of the bloom. During 1996 one such house with a tree of 'Grand Rosa' (U.S. Plant Pat. No. 1,756) was crossed by me in this manner. To pollinate this 'Grand Rosa' tree, I selected bouquets from several sources that season without keeping written details. Upon reaching maturity the fruit from this 'Grand Rosa' tree was harvested and the seeds were removed, cracked, stratified and germinated as a group with the label "42PH11". They were grown as seedlings on their own root in my greenhouse and, upon reaching dormancy, transplanted to a cultivated area of my experimental orchard at Bradford Farms near Le Grand, Calif. in Merced County (San Joaquin Valley). During the summer of 2000, the present variety was selected as a single plant from the group of seedlings described above. Therefore, the variety was developed as a first generation cross using 'Grand Rosa' (U.S. Plant Pat. No. 1,756) plum as the selected seed parent and an undetermined plum as the pollen parent. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its seed parent, 'Grand Rosa' (U.S. Plant Pat. No. 1,756), by being self-unfruitful and by producing plums that are globose to oblate in shape, mostly red in skin color, and yellow with some red bleeding in flesh color but is distinguished therefrom and an improvement thereon by producing plums that are clingstone instead of semi-freestone, that are smoother in skin surface, that are sweeter in flavor, that do not have a tendency to tip crack, and that mature about 3 weeks later.

SUMMARY OF VARIETY

The present plum variety is characterized by a medium size, vigorous, hardy, and usually productive tree. Being self-unfruitful, the present variety requires cross pollinization from another plum that blooms during the mid season, such as 'Blackamber' (unpatented). The present variety's abundance of blossoms and pollen entices strong bee activity to facilitate pollination. The fruit matures under the ecological conditions described during mid August, with first picking on Aug. 11, 2002, but will hang on the tree for nearly twenty more days. The fruit is uniformly large in size, dark red in skin color, clingstone in type, yellow with some red bleeding in flesh color, very firm and crisp in texture, very good in flavor, and holds well in cold storage for more than thirty days.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Aug. 15, 2002, on the original tree during its sixth growing season. All major color code designations are by reference to the Inter-Society Color Council, National Bureau of Standards. Common color names are also used occasionally.

TREE

Size: Medium, reaching and maintaining a height of 11' [3.4 m.] and a spread of 7' [2.1 m.] after six growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright and open.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming plum, such as 'Blackamber' (unpatented).

Bearing: Usually consistent, but some uncertainty exists if inclement weather is encountered during the blooming period.

Trunk:

*Size.*—Medium, reaching a maximum diameter of 2¾" [70 mm.] after the sixth growing season.

*Texture.*—Shaggy.

*Bark color.*—Dark grayish brown [62. d.gy.Br] with Light brown [57. l.Br] crevices streaked throughout.

*Lenticels.*—Approximate Number Per Square Inch: 18. Color: Moderate orange [53. m.O]. Typical Size: ⅛" to ⅜" [3.2–9.5 mm.].

Branches:

*Size.*—Diameter of limb is 1¼" [32 mm.] measured 12" above the secondary fork, typical of *Prunus salicina,* and dependent upon cultural practices and climatic conditions.

*Texture.*—Smooth on first year wood, rough on second year wood, shaggy on older wood.

*Color.*—1st Year Wood Topside: Moderate brown [58. m.Br] where exposed to sunlight. 1st Year Wood Underside: Strong yellow green [117. s.YG]. Older Wood: Dark yellowish brown [78. d.yBr] with some Strong yellowish brown [74. s.yBr] crevices streaked throughout.

*Lenticels.*—Number Per Square Inch: Up to 80. Color: Light yellowish brown [76. l.yBr]. Typical size: 1/32" to 3/16" [0.8–4.8 mm.].

Leaves:

*Size.*—Medium to large. Average Length: 3¾" [95 mm.]. Average width: 1 15/16" [49 mm.].

*Arrangement.*—Alternate.

*Thickness.*—Medium.

*Form.*—Elliptical.

*Apex.*—Acuminate.

*Base.*—Rounded to acute, with an average angle base angle of 90 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 1/12" [12.7 mm.]. Average Thickness: 1/16" [1.6 mm.]. Color: Light yellow green [119. lYG] with Moderate reddish brown [43. m.rBr] tinting if exposed to sunlight.

*Stipules.*—Number: Almost always 2 per leaf. Average Length: ¼" [6.4 mm.]. Color: Brilliant yellow green [116. brill.YG] becoming Dark reddish brown [44. d.rBr] with age.

*Glands.*—Number: 2 to 6 per leaf. Position: Mostly alternate, few opposite, positioned on the petiole and blade. Size: Small. Form: Globose. Color: Strong reddish brown [40. s.rBr].

*Leaf buds.*—Conic.

Flower buds:

*Hardiness.*—Hardy, with respect to central California winters.

*Diameter.*—Typically 3/16" [4.8 mm.] 1 week before bloom.

*Length.*—Typically ⅜ [9.5 mm.] 1 week before bloom.

*Form.*—Not appressed.

*Surface.*—Pubescent.

*Color.*—White [263. White].

Flowers: Perfect, complete, perigynous, usually a single pistil, typically thirty or more stamens, five sepals and petal locations alternately positioned.

*Average flower diameter.*—11/16" [17.5 mm.].

*Number of petals.*—Five, no double blossoms observed.

*Petal shape.*—Circular.

*Petal margin.*—Wavy.

*Average petal diameter.*—7/16" [11.1 mm.].

*Average petal length.*—⅜" [9.5 mm.].

*Petal apex.*—Rounded.

*Petal base.*—Rounded.

*Petal color.*—White [263. White].

*Anther color.*—Brilliant yellow [83. brill.Y].

*Stigma color.*—Light greenish yellow [101. lgy].

*Sepal color.*—Light yellow green [119. lYG].

*Sepal length.*—5/32" [4 mm.].

*Sepal width.*—⅛" [3 mm.].

*Average pistil length.*—⅜" [9.5 mm.].

*Average stamen length.*—5/16" [7.9 mm.].

*Fragrance.*—Moderate.

*Pollen production.*—Abundant.

*Blooming period.*—Medium compared with other varieties, two days before 'Santa Rosa' (unpatented).

*Onset of bloom.*—One percent on Feb. 20, 2002.

*Date of full bloom.*—Mar. 5, 2002.

*Duration of bloom.*—One to two weeks, dependent on ambient temperature.

*Number per cluster.*—3 to 9, average 5.

FRUIT

Maturity when described: Firm ripe, Aug. 15, 2002.
Date of first picking: Aug. 11, 2002.
Date of last picking: Aug. 25, 2002.
Size: Uniform, large.
*Average diameter axially.*—2 5/16" [58.7 mm.].
*Average diameter across suture plane.*—2 5/8" [66.7 mm.].
*Typical weight.*—5.9 ounces [167 grams].
Form: Uniform, symmetrical, somewhat oblate.
*Longitudinal section form.*—Elliptical, compressed axially.
*Transverse section through diameter.*—Circular.
Suture: An inconspicuous line located in a very shallow groove extending from the base and discontinuing at the pistil point.
Ventral surface: Rounded, slightly lipped toward the apex.
Lips: Fairly equal.
Cavity: Flaring, circular, suture showing on one side.
*Depth.*—7/16" [11.1 mm.].
*Breadth.*—1" [25.4 mm.].
Base: Truncate.
Apex: Usually truncate with a small hump just before the pistil point.
Pistil point: An inconspicuous dot.
Stem: Medium.
*Average length.*—3/8" [9.5 mm.].
*Average width.*—3/32" [2.4 mm.].
Skin:
*Thickness.*—Medium.
*Surface.*—Smooth.
*Tenacity.*—Tenacious to flesh.
*Astringency.*—Slight.
*Tendency to crack.*—Very slight.
*Color.*—Very dark red [17. v.d.R] smoothly blending to Dark red [16. d.R] with occasional Moderate yellow [87. m.Y] sun protected areas and small Pale orange yellow [73. p.OY]freckling throughtout.
*Bloom.*—Abundant.
Flesh:
*Color.*—Light yellow [86. l.Y] with a varying degree of Moderate red [1.5. m.R] streaking toward the skin that increases with maturity.
*Surface of pit cavity.*—Covered with short Pale yellow [89. p.Y] fibers that break away from the stone when strongly twisted.
*Amygdalin.*—Moderate.
*Juice.*—Abundant, rich.
*Texture.*—Very firm and crisp, will hang 20 days on tree.
*Fibers.*—Abundant, fine.
*Ripens.*—Fairly even.
*Flavor.*—A blend of medium acid and high sugar, typically 18 to 21 brix.
*Aroma.*—Slight.
*Eating quality.*—Very good.

STONE

Type: Clingstone.
Form: Oval.
Hilum: Narrow, oblong.
Base: Straight.
Apex: Obtusely wedge shaped with a average angle of 110 degrees.
Sides: Equal.
Surface: Rough with no pitting or grooves.
External color of stone: Light grayish yellowish brown [79. l.gy.yBr].
Pit wall color when cracked: Light brown [57. l.Br].
Cavity surface color: Moderate brown [58. m.Br].
Average pit wall thickness: 1/16" [1.6 mm.].
Average width: 5/8" [15.9 mm.].
Average length: 1" [25.4 mm.].
Average breadth: 3/8" [9.5 mm.].
Tendency to split: Slight.
Kernel:
*Form.*—Oval.
*Skin color.*—Pale yellow [89. p.Y] when first cracked.
*Pellicle color.*—Light brownish gray [63. l.brGy].
*Vein color.*—Light brownish gray [63. l.brGy].
*Taste.*—Bitter.
*Viable.*—Yes.
*Average width.*—7/16" [11.1 mm.].
*Average length.*—9/16" [14.3 mm.].
*Amygdalin.*—Abundant.

USE

Market: Fresh market and long distance shipping.
Keepinq quality: Excellent. Fruit quality observed to remain in good condition in after 30 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to its seed parent, 'Grand Rosa' U.S. Plant Pat. No. 1,756), by being self-unfruitful and by producing plums that are globose to oblate in shape, mostly red in skin color, and yellow with some red bleeding in flesh color but is distinguished therefrom and an improvement thereon by producing plums that are clingstone instead of semi-freestone, that are smoother in skin surface, that are sweeter in flavor, that do not have a tendency to tip crack, and that mature about 3 weeks later.

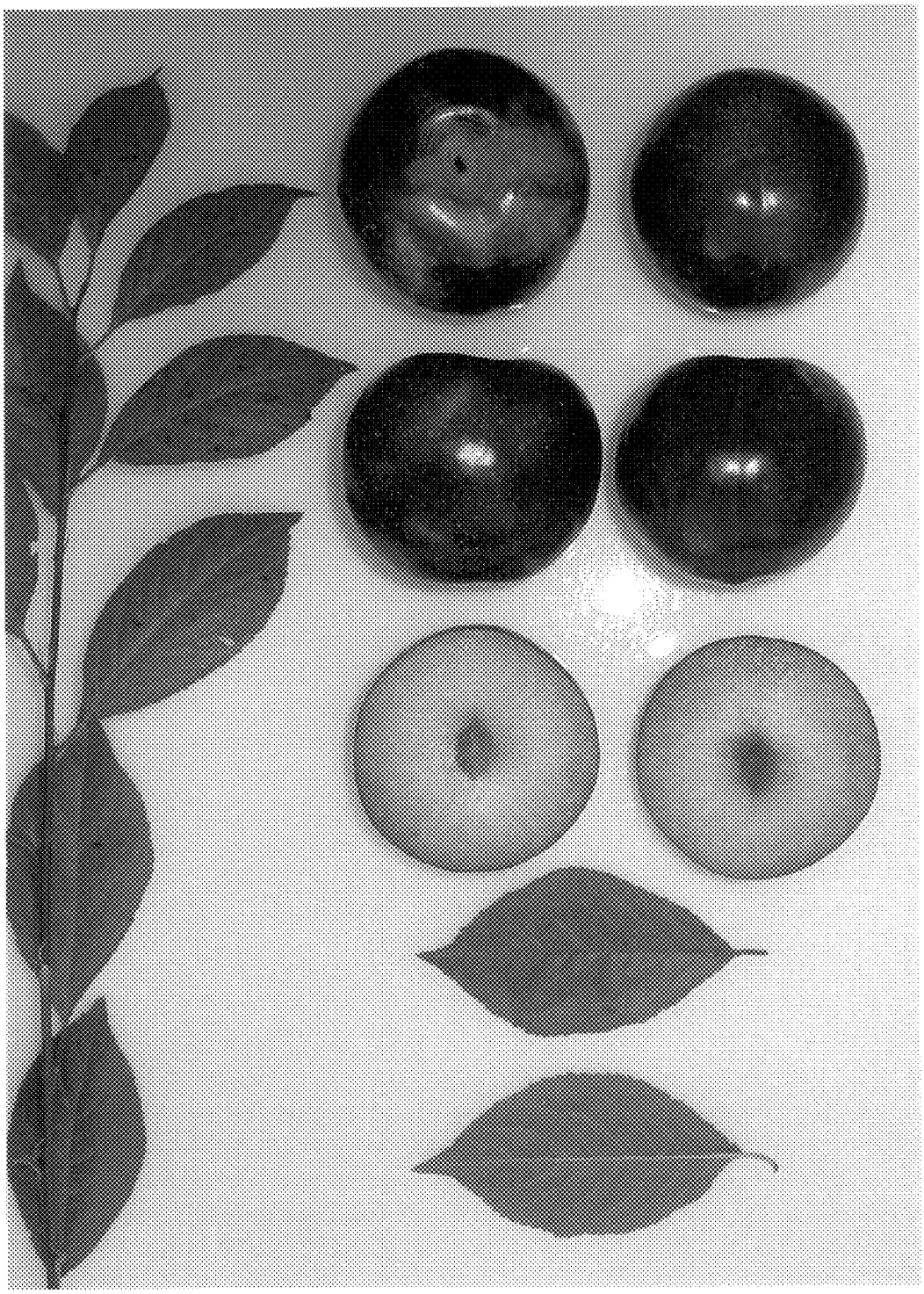

* * * * *